US008241236B2

(12) United States Patent  
Yardley

(10) Patent No.: US 8,241,236 B2  
(45) Date of Patent: Aug. 14, 2012

(54) APPARATUS FOR CLEANING A NASAL CAVITY

(75) Inventor: Mark J. Yardley, Beaver, UT (US)

(73) Assignee: Y B Innovations, LLC, Logan, UT (US)

(*) Notice: Subject to any disclaimer, the term of this patent is extended or adjusted under 35 U.S.C. 154(b) by 381 days.

(21) Appl. No.: 12/408,654

(22) Filed: Mar. 20, 2009

(65) Prior Publication Data

US 2009/0240239 A1 Sep. 24, 2009

Related U.S. Application Data

(60) Provisional application No. 61/038,476, filed on Mar. 21, 2008.

(51) Int. Cl.
*A61M 35/00* (2006.01)
(52) U.S. Cl. ............................. 604/2; 424/434; 600/572
(58) Field of Classification Search .................. 604/1–3; 424/434; 600/572
See application file for complete search history.

(56) References Cited

U.S. PATENT DOCUMENTS

| 1,381,829 A | 6/1921 | Hartman |
| 3,508,547 A | 4/1970 | Deuschle |
| 3,818,911 A * | 6/1974 | Fournier ............................ 604/1 |
| 5,229,061 A | 7/1993 | Van Dyke et al. |
| 5,326,603 A | 7/1994 | Van Dyke et al. |
| 5,826,600 A | 10/1998 | Rowe et al. |
| 6,080,783 A | 6/2000 | Davidson et al. |
| 6,277,090 B1 | 8/2001 | Crawford, Jr. |
| 6,516,947 B1 | 2/2003 | Van Dyke et al. |
| 2003/0173236 A1 | 9/2003 | Van Dyke et al. |
| 2006/0151915 A1 | 7/2006 | Dyke et al. |

OTHER PUBLICATIONS

International Search Report and Written Opinion from PCT/US2009/037897, dated May 18, 2009, 7 pages.
International Preliminary Report on Patentability from PCT/US2009/037897, dated Sep. 30, 2010.
ZICAM Allergy Gel Swabs, http://www.zicam.com/products/allergy_gelswabs, Believed to be dated prior to Apr. 5, 2007.
Pro-Swab, http://www.gmpllc.net/Specs.html, Great Midwest Packaging, LLC, believed to be dated prior to Apr. 5, 2007.

* cited by examiner

Primary Examiner — Melanie Hand
(74) Attorney, Agent, or Firm — Workman Nydegger

(57) ABSTRACT

A nasal cleaning apparatus is described that includes a grip portion and a cleaning portion. The grip portion may include a handle and one or more gripping members attached to the handle. Such gripping members may facilitate rotation of the grip portion or other handling of the apparatus. The cleaning portion includes a head that is attached to a nasal cleaning cloth. The nasal cleaning cloth is disposed around and attached to the head, and is formed of a flexible, anti-microbial material. An extension member connects the cleaning portion to the grip portion. The nasal cleaning apparatus may be disposable and/or modular to facilitate multiple uses of all or only portions of the apparatus.

12 Claims, 3 Drawing Sheets

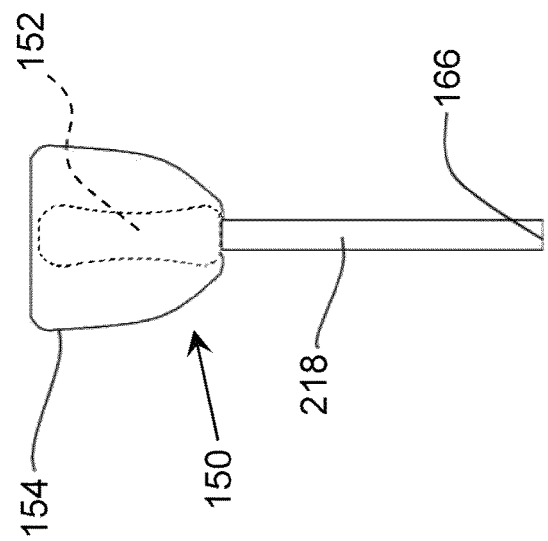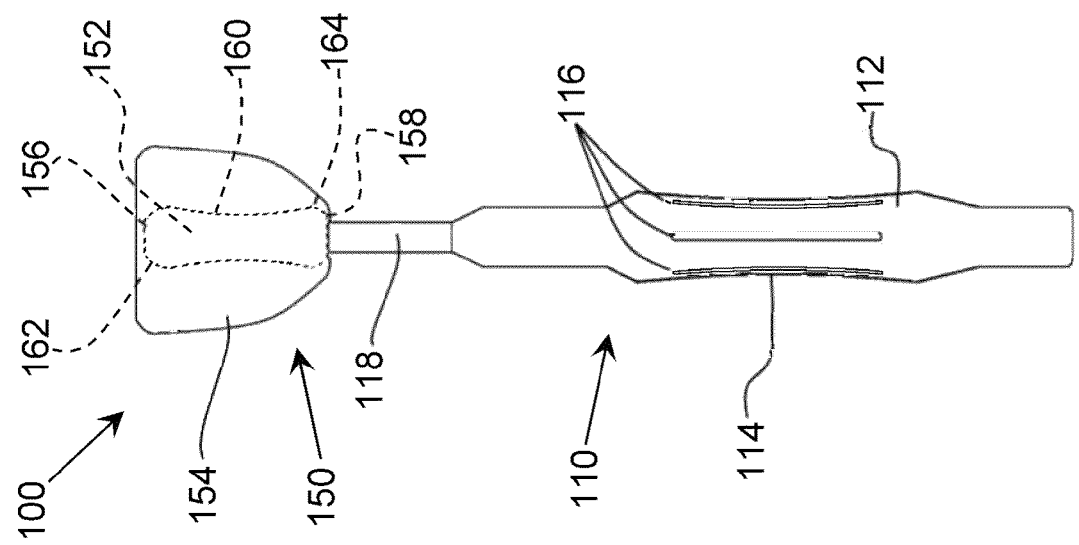

APPARATUS FOR CLEANING A NASAL CAVITY

CROSS-REFERENCE TO RELATED APPLICATIONS

This application claims the benefit of, and priority to, U.S. Provisional Application Ser. No. 61/038,476 which was filed on Mar. 21, 2008 and is entitled "NASAL SWAB," which application is hereby expressly incorporated by this reference in its entirety.

BACKGROUND OF THE INVENTION

1. The Field of the Invention

Exemplary embodiments of the invention relate to devices and methods for cleaning the nose. More particularly, exemplary embodiments of the invention relate to devices and methods for cleaning nasal cavities to remove substances therein.

2. The Relevant Technology

Human beings and other animals generally suffer from all sorts of ailments which can be treated or prevented by taking proper remedial or preventative measures. For example, a person who comes into contact with dust, smoke, smog, pollen, pet danger, debris, germs, bacteria, a virus, and the like may suffer from allergies the common cold, the flu, a bacterial infection, or other ailments. However, if these substances and organisms can be removed in a timely manner, the person may be able to prevent such ailments from occurring, or at least minimize the effects of such substances.

Removing these substances and organisms is oftentimes not an easy task, particularly inasmuch as dust, bacteria and viruses may be received in a bodily orifice, such as the nostrils of the nose, and then internalized such that regular cleaning of the body of the person will not remove these ailment causing materials. However, before such materials are fully internalized, they may enter the nose and attach to the walls of the nasal cavity and/or hairs or other items therein. When such materials attach to the walls of the nasal cavity, or are internalized after entering the nasal cavity, the materials may be difficult to remove even if the person blows his or her nose. If, however, such attached materials can be quickly and easily removed, a person may be able to prevent such materials from causing an ailment, and/or may be able to remedy an ailment already being suffered. By quickly and efficiently removing such materials, a person may thus avoid or minimize colds, the flu, allergies, and the like. By minimizing such ailments, people may, for example, lose less time at work, and/or save money that would otherwise be spent on over-the-counter or prescription drugs, and generally reduce the strain on their immune systems.

Accordingly, what is desired is an apparatus that safely, efficiently and sanitarily removing debris and other materials from inside of a person's nose.

BRIEF SUMMARY OF THE INVENTION

Exemplary embodiments of the invention relate to apparatus and assemblies for cleaning nostrils and nasal cavities. More particularly, exemplary embodiments relate to devices and methods for cleaning nasal cavities to remove dust, pollen, germs, and other substances from therein.

According to one embodiment of the present invention, an apparatus is disclosed for cleaning a nasal cavity of a user. The apparatus may include a grip and a head attached to the grip. An anti-microbial cleaning cloth may be attached to the head and can be configured to be inserted into the nostril of a user, along with the head, to remove debris from the nasal cavity of a user. The apparatus may also include an extension member disposed between the grip and the head, and which attaches the head to the grip. The extension member may include a neck for attaching the head to the grip.

The anti-microbial cleaning cloth may be attached to the head in any suitable manner. For example, the cloth may be folded or wrapped around the head, or may be fitted therearound, deposited thereon, or integrally formed as a portion thereof. The head may also have a substantially semi-spherical distal end and a contoured external surface. The contoured surface may have multiple different diameters along the length thereof. For example, a middle portion may have a concave contour while distal and proximal ends have convex contours. The grip may also have one or more gripping members to facilitate handling of the grip. For instance, a contour may act as a gripping member, or one or more ridges may be formed as all or part of the gripping members. The ridges themselves may extend along at least a portion of the elongate length of the grip, and may extend along a portion having a concave contour.

According to another embodiment, a nasal cavity cleaning apparatus is disclosed that includes a handle and a disposable cleaning portion connected to the handle. The disposable cleaning portion is sized so that it is easily insertable into a nostril of a user, and includes an anti-microbial cleaning cloth adapted to remove materials from an interior of a nostril. An extension is positioned between the cleaning cloth and the handle, and is adapted to displace the cleaning cloth from the handle to allow a user to easily and comfortably insert the cleaning cloth into the nostril. A head may also be mounted to the extension and to the anti-microbial cleaning cloth.

The disposable cleaning portion may be selectively separable from the handle, or may be at least partially integral therewith. For example, the extension member may be integral with the handle. Accordingly, both the handle and the cleaning portion may be disposable, and may be collectively disposable. The handle can be ergonomically formed to allow handling and manipulation of the nasal cavity cleaning apparatus.

According to another embodiment, a nasal cleaning apparatus includes a grip portion, an extension member, and a cleaning portion. The grip portion includes a handle and one or more gripping members that are attached to the handle and facilitate rotation of the grip portion. The cleaning portion includes a head that is contoured with a rounded distal end, and further includes a nasal cleaning cloth disposed around and attached to the head. The nasal cleaning cloth is formed of a flexible, anti-microbial material. The extension member connects the cleaning portion to the grip portion. Additionally, the extension member may be a separate component, or may be formed as part of the grip portion or part of the cleaning portion. Accordingly, an apparatus is described that can optionally operate as a nasal swab and at least partially be inserted into a nostril and clean materials therefrom. such a swab includes an anti-microbial tip or cloth that performs the cleaning.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope, nor are the drawings necessarily drawn to scale. The invention will be described and explained with additional specificity and detail through the use of the accompanying drawings in which:

FIG. 2 illustrates a side view of an exemplary apparatus for cleaning a nasal cavity and which has gripping members on a handle of the apparatus.

FIG. 3 illustrates an embodiment of a replaceable and/or disposable nasal cleaning portion of an apparatus for cleaning a nasal cavity, according to another embodiment of the present invention.

DETAILED DESCRIPTION OF SOME PREFERRED EMBODIMENTS

Exemplary embodiments of the invention relate to apparatus and assemblies for cleaning nasal cavities. In particular, exemplary embodiments of the present invention relate to a nasal cleaning apparatus which may be reusable and/or disposable, or which may have reusable and/or disposable components.

Reference will now be made to the drawings to describe various aspects of exemplary embodiments of the invention. It is understood that the drawings are diagrammatic and schematic representations of such exemplary embodiments, and are not limiting of the present invention, nor are they necessarily drawn to scale. The drawings thus provide one scale; however, no inference should therefore be drawn from the drawings that any dimension of the invention or element is required. In the following description, numerous specific details are set forth in order to provide a thorough understanding of the example embodiments of present invention. It will be obvious, however, to one of ordinary skill in the art that the present invention may be practiced without these specific details.

Figure 1:
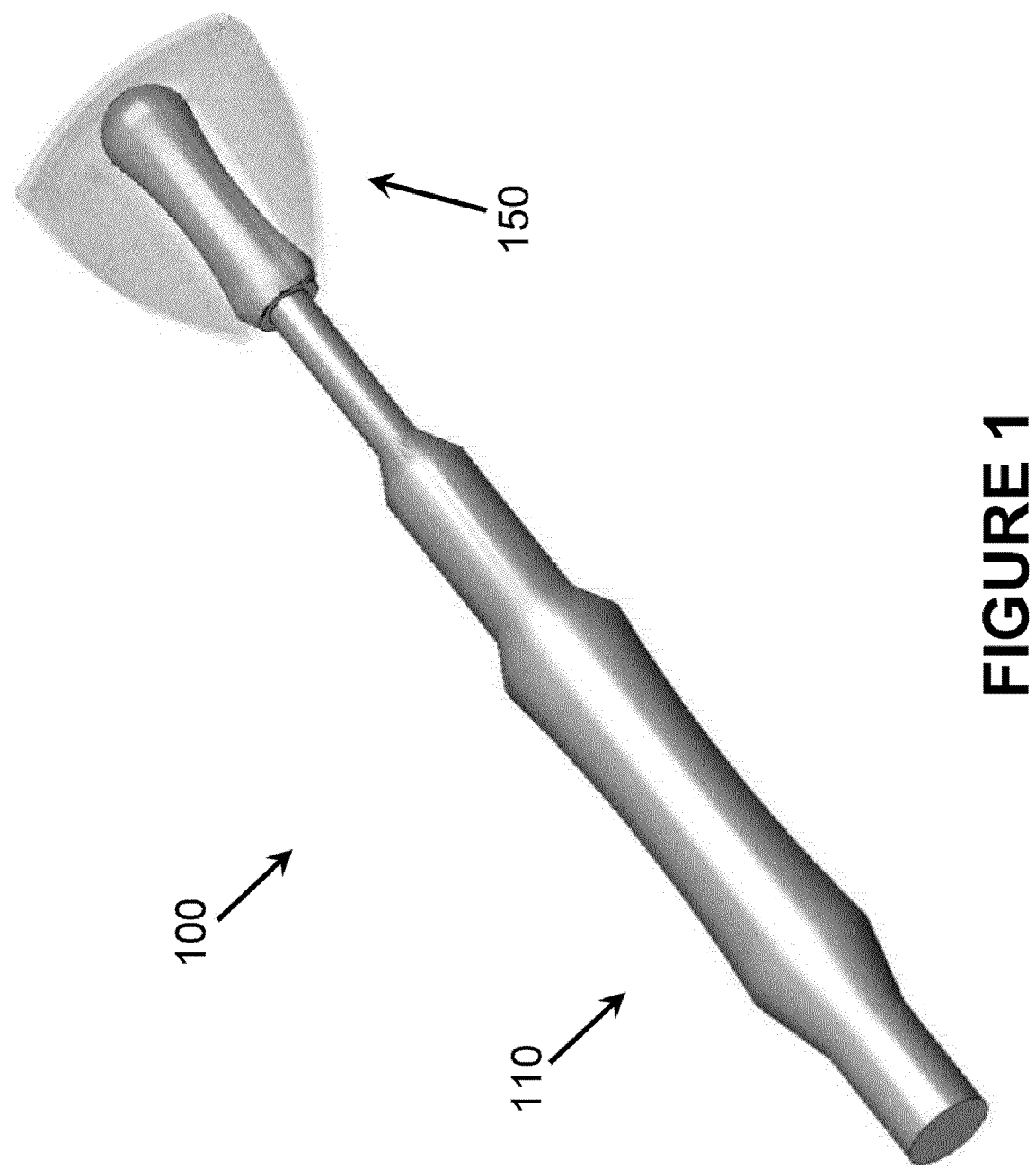
FIG. 1 illustrates a perspective view of an exemplary apparatus for cleaning a nasal cavity, and which can be inserted into the nostril of a user and remove materials therefrom.

Referring now to FIG. 1, an exemplary apparatus 100 for cleaning a nasal cavity is illustrated according to some aspects of the present invention. In FIG. 1, for example, apparatus 100 includes a grip portion 110 and a cleaning portion 150. Any suitable grip portion 110 and/or cleaning portion 150 may be used. By way of example and not limitation, grip portion 110 may thus include a handle, or other mechanism for gripping or handling apparatus 100, while cleaning portion 150 may be or include, a swab, cleaning cloth, head, or other type of portion used for cleaning the inside of a nasal cavity and/or may be a combination of different components.

The embodiment illustrated in FIG. 1 is an example of a suitable apparatus 100 for cleaning inside of a user's nose. For example, cleaning portion 150 may extend from grip portion 110 and be used to clean the interior surfaces of the nostrils to keep them clean and free of dust, nasal discharge, mucous, waste, debris, or any other particles or organisms which may become lodged therein.

In the particular embodiment illustrated in FIG. 1, cleaning portion 150 and grip portion 110 are connected and operate together for cleaning of the inside of the user's nostrils. For example, a user can grab a hold of grip portion 110 with the user's hand, fingers, and/or finger tips, and then extend cleaning portion 110 into the user's own nostril, or into the nostril of another. When inside the nostril, cleaning portion 110 can be moved around and/or rotated so as to contact and collect debris and other materials therein. For example, cleaning portion 110 can be rotated as it is placed against the walls of the nasal cavity to clean off any debris lodged against such walls.

In the illustrated embodiment, the tip of cleaning portion 150 has a generally rounded configuration. One feature of such a configuration is that the rounded taper on the tip can allow cleaning portion 110 to safely and comfortably be inserted into the nostril, and it can then be rotated within the nostril to more effectively reach and clean the nasal cavity. According to one embodiment, cleaning portion 150 is configured to rotate by manual means (e.g., the user manually rotating cleaning portion 150 or apparatus 100), or by electrical or mechanical means. For instance, apparatus 100 may include an electric adapter or battery and a motor (not shown) which causes cleaning portion 150 to rotate. In this manner, by turning on the motor, the tip of cleaning portion 150 can automatically rotate within the nostril to effectively clean the nostril and remove debris therefrom. Alternatively, the motor can cause cleaning portion 150 to vibrate or to vibrate and rotate.

In another embodiment, apparatus 100 does not have a motor or other mechanical or electrical means for rotation. Instead, the user can rotate grip portion 110 in his/her hand or fingers to thereby also rotate apparatus 100. In still another embodiment, a non-motorized nasal cleaning apparatus can include manual rotation means therein which can be powered by the user to rotate cleaning portion 150 without rotating grip portion 110. For instance, a rotary track wheel (not shown) may be included within, or adjacent to, grip portion 110 which can be rotated by the user's fingers. The track wheel can then be connected to gearing or other linkages which link the track wheel to cleaning portion 150 thereby causing cleaning portion 150 to rotate as the track wheel is rotated. As another example, a manual rotation means may include a wind-up feature with a resilient member that stores energy. When that stored energy is released (e.g., by pressing a button), the energy can be used to rotate cleaning portion 150.

Turning now to FIG. 2, it can be seen that grip portion 110 and cleaning portion 150 can include a variety of optional components. In the illustrated embodiment, for instance, grip portion 110 includes a handle 112 that where user holds onto apparatus 100, and which allows the user to grasp, handle, manipulate, and/or maneuver apparatus 100. Handle 112 may have any suitable shape and configuration that provides the user with such ability. For example in the illustrated embodiment, handle 112 is contoured and has a concave contour 114 along the outer perimeter of all or a portion of handle 112. Concave contour 114 is ergonomically formed to provide a mechanism by which the user can comfortably grasp, handle, and use apparatus 100. Of course, in other embodiments, other types of contours or other ergonomically desirable forms may be utilized, or no contour or other ergonomically desired shape is used. For instance, in some embodiments, bumps and/or depressions may be provided, and any or all of such structures may facilitate manipulation and handling of apparatus 110 by a hand, finger, and/or finger tip of a user.

In one embodiment, handle 112 includes one or more gripping members 116. Gripping members 116 may have any desirable shape or form, and can provide any of a number of different features. For example, according to one embodiment gripping members 116 help to prevent slippage of a user's fingers or finger tips while the user is handling apparatus 100. Thus, gripping members 116 can help to create a non-slip or substantially non-slip surface on handle 112. Additionally, gripping members 116 can allow the user to more easily rotate or otherwise manipulate apparatus 100 in a desired manner. For example, as discussed herein, it may be desirable to rotate grip portion 110 so as to cause cleaning portion 150 to rotate as it cleans debris or other materials from the inside of a person's nostril. Gripping members 116 may provide a tactile surface on which the user can create pressure with his or her fingers, thereby more easily manipulating and rotating apparatus 100.

Gripping members 116 may have any suitable design, form and/or construction. For example, in one embodiment, gripping members 116 include one or more ridges extending along at least a portion of the elongate length of handle 112. Such ridges may be integrally formed or may be formed separately and affixed to handle 112 with an adhesive, or may even be formed on a sleeve or other component that is thereafter attached around handle 116. Furthermore, any number of such ridges or gripping members 116 may be utilized. In FIG. 2, for example, three gripping members 116 are illustrated on one side of handle 114. As will be appreciated, another three gripping members 116 may also be provided on the opposite side of handle 114, although such number of gripping members is merely exemplary, and more or fewer gripping members 116 may be provided.

Gripping members 116 may also take other shapes and forms. For example, in one embodiment, a gripping member may merely take the form of the concave contour 114. In other embodiments, one or more bumps, depressions, channels, circumferential or orthogonal ridges, or any combination thereof may be utilized as a gripping member 116 to facilitate handling, manipulation and/or use of apparatus 100. Gripping members 116 may also take the form of a non-slip surface, such as a sleeve made of rubber or another non-slip material that is then attached to handle 114.

Handle 116 allows the user to grasp and use apparatus 100, and may have any desirable size and shape, and may further be connected directly or indirectly to cleaning portion 150. In the embodiment illustrated in FIG. 2, grip portion 110 includes an extension member 118 that connects to, and extends from, handle 112 and connects to cleaning portion 150. Extension member 118 can act as a neck that facilitates attachment between handle 114 and cleaning portion 150, and it will be appreciated in view of the disclosure herein that extension member 118 may be integrally formed with handle 114, or may be formed separate therefrom. Indeed, in one embodiment all or a portion of extension member 118 may be selectively detachable from handle 112 and/or cleaning portion 150.

Extension member 118 may also have any desirable length, shape, or form. According to one aspect, extension member 118 may have a substantially uniform cross-section and/or may have a length calculated to allow the user of apparatus 100 to grasp handle 114 and easily and comfortably place cleaning portion 150 into the user's nostril. For instance, when a user places his or her fingers on handle 114 (e.g., at gripping members 116), extension member displaces cleaning portion 150 from the user's fingers so that the user can easily and comfortable insert cleaning portion 150 into the user's nose and clean the nasal cavities therein. In one example, handle 114 may be approximately two and one-half inches in length, and extension member 118 may extend approximately seven-eighths inch. Not all of extension member 118 may be visible, however, and a portion of extension member 118 may extend into cleaning portion 150. Alternatively, extension member 118 may connect directly to cleaning portion 150 without extending therein and/or may have a variable cross-section across its length.

With continued reference to FIG. 2, apparatus 100 may also include a cleaning portion 150 that is directly or indirectly connected to grip portion 110. In the illustrated embodiment, cleaning portion 150 is constructed and adapted to provide a sanitary and hygienic mechanism for cleaning debris or other materials from the inside of the use's nostril. Cleaning portion 150 may have any suitable construction, design, and form, accordingly the embodiments illustrated and described herein are merely embodiments and are not necessarily limiting of the present invention.

In the embodiment illustrated in FIG. 2, cleaning portion 150 includes a head 152 and a nasal cleaning cloth 154. In particular, head 152 is connected to extension 118 of grip portion 110, and nasal cleaning cloth 154 is wrapped or otherwise placed around the exterior of head 152. Head 152 thus provides an internal structure that supports nasal cleaning cloth 154 as nasal cleaning cloth 154 is inserted into the nose of a user and is used to clean debris, pollen, dust, and/or other materials therefrom.

With more particular attention to the exemplary embodiment illustrated in FIG. 2, head 152 is illustrated in phantom lines to depict that it is positioned inside of nasal cleaning cloth 154. It should be appreciated in view of the disclosure herein that such is not always necessary. For example, in one embodiment, head 152 may be integrally formed with nasal cleaning cloth 154, such that the outer surface of head 152 is used to clean the inside of a user's nostril. Accordingly, nasal cleaning cloth 154 may be a material that is separate from, but attached to, head 152, or it may be integral therewith.

Head 152 may be designed as a support member that facilitates attachment of nasal cleaning cloth 154 to grip portion 152, and may also support nasal cleaning cloth 154 while it is within the nostril of a user. Head 152 may thus have any suitable shape or form that provides these or other features. Head 152 may further be shaped in any manner that allows it to be inserted into the nostril of a user, and may have a shape that facilitates its use with a wide variety of nostril sizes and shapes. In the illustrated embodiment, for instance, a contoured and tapered configuration is illustrated that includes a plurality of different contour portions. For example, in the illustrated embodiment, head 152 includes a middle portion having a substantially concave portion 160. As illustrated in FIG. 2, for example, concave portion 160 includes an inwardly curving surface. On either side of concave portion 160, such as at distal end 156 and proximal end 164, there may be convex portions 162, 164. For instance, at distal end 156, convex portion 162 may be have a generally semi-spherical shape. The semi-spherical shape tapers inward toward distal end 156. Distal end 156 is the first portion of apparatus 100 that is inserted into a user's nose. Thus, by tapering outward from distal end 156, head 152 facilitates easy insertion and advancement of apparatus 100 at least part way into the user's nostril. Head 152 need not always have such a construction, however and may have any number of different shapes, forms and/or contours.

As noted previously, the shape of head 152 is merely one example of a head usable as all or a part of cleaning portion 150, and head 152 may have any other desired shape or form. For example, in one embodiment, head 152 may have only a single contoured portion. For instance, head 152 may be generally spherical or balloon-shaped such that substantially all surfaces are convex. Alternatively, head 152 may have only one, or more than one, concave surface, may have non-contoured and/or tapered portions, may have any combination of the above, or any other suitable shape.

To further facilitate cleaning and removal of debris from the inside of the nostril of a user, a nasal cleaning cloth 154 may be attached to head 152. Nasal cleaning cloth 154 is, in the illustrated embodiment attached to the exterior of head 152. Nasal cleaning cloth 154 may also be a pliable material that can be shaped as desired by the user. Thus, apparatus may be produced such that the shape of nasal cleaning cloth 154 essentially conforms to the shape of head 152, although it is not necessary to do so. In some embodiments, nasal cleaning cloth 154 may be a more rigid material that is formed around, or slipped onto, head 152, or it may have any other suitable form. In one example, for instance, nasal cleaning cloth 154 is a flexible material that is formed separate from head 152, and is thereafter wrapped thereon.

In one method for manufacturing apparatus 100, nasal cleaning cloth 154 may be initially cut or otherwise formed into a square or diamond shaped piece of cloth. To attach nasal cleaning cloth 154 to head 152, nasal cleaning cloth 154 may first be folded along a diagonal to form a triangular shape. Head 152 may be placed on the interior of nasal cleaning cloth 154, and may be positioned proximate the fold line. With head 152 in that position, cloth 154 can be wrapped, folded, or draped around head 152 and the apex of the formed triangle can be secured to proximal end 158 of head 152. In one example embodiment, head 152 has an opening (not shown) at proximal end 158, and portions of nasal cleaning cloth 154 can be tucked into the opening. Grip portion 110 may then be placed in the opening of head 152 to further secure nasal cleaning cloth 154 therein. In addition, or in the alternative, an adhesive may also be used to secure nasal cleaning cloth 154 to head 152 at proximal end 158 and/or at distal end 156, or at portions between distal end 156 and proximal end 158. An adhesive or other attachment mechanism may also be used to secure head 152 to extension 118 or to grip portion 110.

Figure 4:
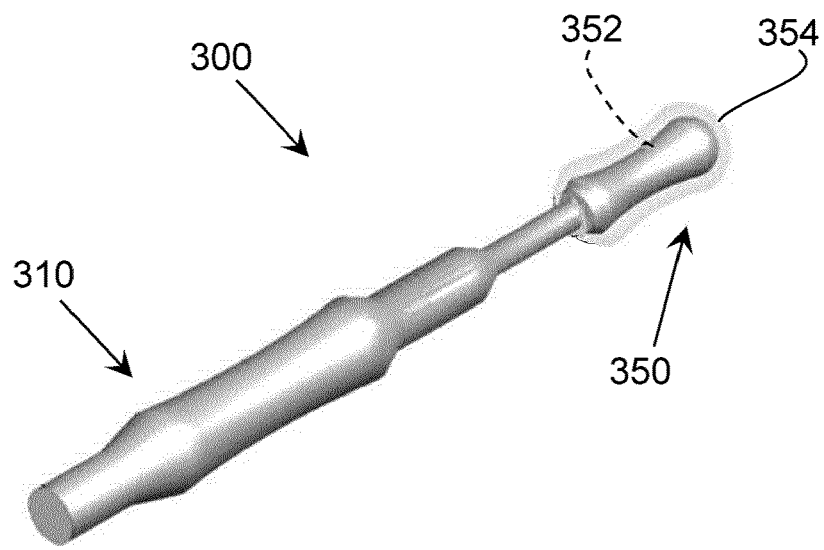
FIG. 4 illustrates an alternative embodiment of an exemplary apparatus for cleaning a nasal cavity.

Securing nasal cleaning cloth 154 in this manner or any other suitable manner can allow nasal cleaning cloth 154 to be generally formed such that it is supported by head 152, and optionally has a shape that generally conforms to that of head 152, although it is not necessary to do so. For instance, when the apex of the triangle formed by folding nasal cleaning cloth 154 is secured to proximal end 158 of head 152, the triangles may form around head 152 in a manner that does not necessarily conform to the shape of head 152. FIGS. 1-3, for example, illustrates a nasal cleaning cloth 154 that is placed around a head 152, but does not necessarily conform to the shape of head 152. Alternatively, FIG. 4 illustrates a nasal cleaning cloth 354 which does substantially conform to the shape of head 352. It will be appreciated in view of the disclosure herein, that the shapes of a nasal cleaning cloth as described herein—both before and after attachment to a head or other component of a nasal cleaning apparatus—are merely exemplary and that other shapes, forms, and attachment mechanisms or methods are contemplated within the scope of the present invention.

The various components of a nasal cleaning apparatus 100 according to the present invention can be made from any of numerous different materials, and can be formed in any suitable manner. For example, nasal cleaning cloth 154 can be formed from any suitable material that would allow and/or facilitate removal of debris and other material from inside a nasal cavity. In one example, nasal cleaning cloth 154 is formed from an anti-microbial material and/or a sterilized material. One feature of such materials is that they can be placed into the nose and clean out materials therein, with reduced risk of introducing additional infective materials or organisms that might cause allergies, the common cold, or the flue, thereby reducing the effectiveness thereof. Any suitable anti-microbial or sterilized material may be utilized. For instance, a microfiber anti-microbial material may be used. In another embodiment, a nasal cleaning cloth 154 may be a fabric which is resistant to microbes and/or bacteria, or which has been treated with an anti-microbial compound. Additionally, or in the alternative, nasal cleaning cloth 154 can be medicated to allow medicine to be applied to the nasal cavity.

In one embodiment, nasal cleaning cloth 154 is made of a soft material so as to gently adhere to material in the nostrils and to safely clean the nostrils. In another embodiment, nasal cleaning cloth 154 is made of a flexible material which is at least partially rough and/or has pores or cavities formed therein (e.g., a mesh material). Such a material may allow nasal cleaning cloth 154 to rub against the interior surface of the nasal cavity and more easily dislodge debris attached thereto, and the pores or cavities may provide space within nasal cleaning cloth 154 to collect and hold such debris. In another embodiment, the tip is made of a rigid material which will effectively rub against materials in the nostrils and dislodge them. Optionally materials of differing levels of rigidity are used to both dislodge materials and to cause materials to adhere to the cleaning portion. In short, any material, or combination of materials, may be used which, when inserted into the nostril, will help remove and eliminate germs, bacteria, dust, pollen, viruses, mucous, or any other type of substance of any kind which may be found within the nose, nostrils, or nasal cavities and which would be beneficial to remove. Such material may also be configured to be washed for repeated uses. For example, after a use, a user may run cleaning portion 150 under water to clean nasal cleaning cloth 154 so that it can be used on other occasions. In one embodiment, cleaning portion, including nasal cleaning cloth 154, is adapted to be cleaned and reused. For example, nasal cleaning cloth 154 may be made of a material (e.g., polymeric material, organic-based material, etc.) that can hold up under cleaning as it is washed with for example, a soft soap and warm water.

Head 152 and grip portion 110 may also be formed of any suitable material. In one example, head 152 is formed of a material which sufficient rigidity to provide support nasal cleaning cloth 154 as cleaning portion 150 is inserted into a nostril and engages the interior surface of the nostrils to clean debris and other materials therefrom. For example, a foam material may be used. Such a material may be sufficiently rigid to support nasal cleaning cloth 154 and to provide a surface around which nasal cleaning cloth 154 can be positioned or formed, but may also be somewhat pliable such that it yields and does not easily damage tissue within the nasal cavity. Of course, other materials may also be used, including polymers, rubber, composites, organic materials, metals, alloys, or other materials or combinations thereof. Handle 114 and/or extension 118 may also be formed of similar materials. For instance, handle 114 and extension 118 may be integrally formed of a substantially rigid polymeric material. Alternatively, handle 114 and extension 118 may be separately formed and/or be made from a foam, rubber, composite, organic, metal, alloy, or other material, or a combination thereof.

As further evident at least the embodiments depicted in, and described relative to, FIG. 2 and FIG. 3, in some embodiments a nasal cleaning apparatus 100 may be fully or partially reusable and/or disposable. For instance, FIG. 2 illustrates an example apparatus 100 which may be fully disposable. In particular, apparatus 100 may be designed and constructed to for a single use or for multiple uses, after which it should be discarded in its entirety. Alternatively, the embodiment illustrated in FIG. 3 shows an example portion of apparatus 100 that may be utilized when only a portion of apparatus 100 is intended to be disposable.

For instance, in the embodiment illustrated in FIG. 3, a cleaning portion 150 that includes an extension 218. In this embodiment, extension 218 may be selectively removable from handle 114 (FIG. 2). This may allow, for example, handle 114 to be reused with any number of different cleaning portions 150, and each disposable cleaning portion 150 can be discarded after one or more uses.

To facilitate selective detachment with handle 114, cleaning portion 150 may have a mechanism for providing selective attachment to, and detachment from, handle 114. For example, threads (not shown) may be formed on a proximal end 166 of extension 218 and configured to mate with corresponding threads found in handle 114. It will be appreciated, however, that any other suitable connection mechanism may be used, including lock fits, interference fits, clasps, clamps, or any other connection mechanism or combination thereof.

Furthermore, extension 218 may itself also be reusable apart from head 152 of cleaning portion 150. For example, it may also be possible to remove head 152 from extension portion 218 in the event that extension 218 or head 152 becomes damaged or worn. Thus, a nasal cleaning apparatus according to the present invention can have a modular construction allowing any of numerous components to be selectively attached and detached as desired.

It will be appreciated that one feature of removable and/or replaceable components is that the same components (e.g., handle, extension, head, etc.) may be used multiple times to safely and efficiently clean the nostrils. This in turn reduces the cost of the product inasmuch as an entirely new product is not needed for each subsequent use. Instead, in embodiments having a disposable head, only the head and/or nasal cleaning cloth need be obtained for each use or for limited uses. It will also be appreciated that by having a reusable handle or grip that is not replaced each time, the grip can be cost-effectively engineered for comfort and suitability for continued use. For instance, as discussed above, the handle may be engineered to have a mechanical and/or electrical system for rotating the cleaning portion. The grip may also be made of soft-grip materials to increase the comfort of use and/or contoured for a comfortable grip.

FIG. 4 illustrates another embodiment of an example nasal cleaning apparatus 300 similar to that in FIG. 1, but having a nasal cleaning cloth 354 of a different shape. In particular, in the embodiment illustrated in FIG. 4, nasal cleaning cloth 354 is attached to, or otherwise substantially encompasses, head 352. Whereas FIG. 1 illustrates a nasal cleaning cloth that does not necessarily conform to the full shape of the head of the cleaning portion, FIG. 4 illustrates that nasal cleaning cloth 354 can be made to conform generally to the shape of head 352. In this embodiment, nasal cleaning cloth 354 is illustrated as partially transparent so as to show head 352, and nasal cleaning cloth 354 is shaped to have concave and convex sections generally corresponding to concave and convex curves on head 352. To conform to the shape of head 352, it is not necessary, however, that all contours of head 352 be matched by nasal cleaning cloth 354. For example, in the illustrated embodiment, the concave curve towards the middle of nasal cleaning cloth 354 could be less concave, could not taper at all, or could be convex, and nasal cleaning cloth 354 may still substantially conform to the shape of head 352.

As will also be appreciated in view of the disclosure herein, while FIG. 4 illustrates an embodiment similar to that of FIG. 1, head 352 and/or nasal cleaning cloth 354 may equally be used with a modular or removable apparatus such as that illustrated in FIG. 3. Accordingly, components, structures, and materials of any embodiment herein may be combined with the other disclosed embodiments.

In view of the foregoing, it will be appreciated that a nasal cleaning apparatus of the present invention may be manufactured or produced to have any of a variety of different sizes and configurations. In one example, the grip portion of the apparatus may have a total length of approximately three and one-third inches, and a maximum width of approximately three-eighths inches. Additionally, the head of the cleaning portion can have a length of approximately three-quarter inches and a maximum diameter of about one-quarter inch. At this size, the head can easily be inserted into a nostril of a typical user with tolerances to allow the user to rotate the cleaning portion as needed to clean the debris, dust, mucosal buildup, bacteria, viruses, pollen, waste, discharge, or any other materials therefrom. The nasal cleaning cloth 154 that is attached to the head may also have any desirable size. For instance, in one embodiment, the nasal cleaning cloth is formed of an anti-microbial material that is diamond-shaped and approximately one and one-half inches along each side. This allows the nasal cleaning cloth to be folded around the head while still providing sufficient cleaning material to ensure an effective cleaning of the interior of a user's nostrils.

Figure 5:
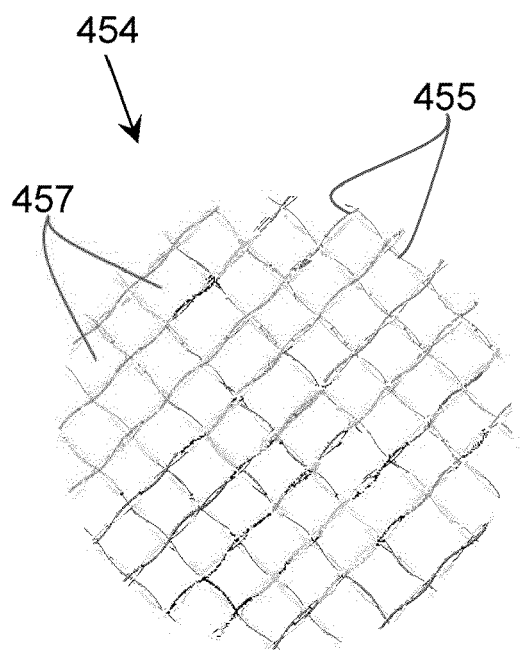
FIG. 5 illustrates is a close-up view of an exemplary nasal cleaning cloth.
Figure 6:
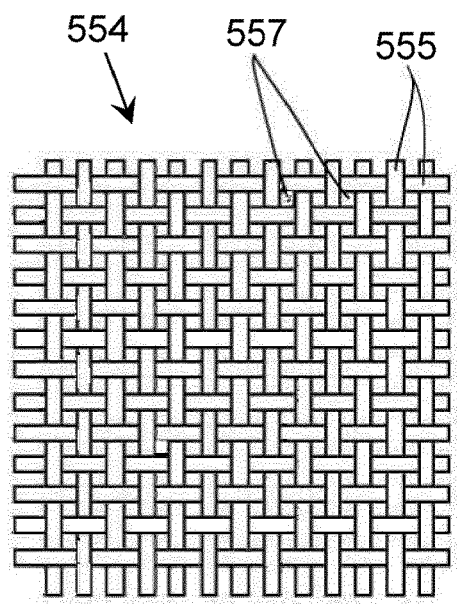
FIG. 6 illustrates a close-up view of an alternative exemplary nasal cleaning cloth.

Turning now to FIGS. 5 and 6, close-up views of exemplary materials that may be used in connection with at least the nasal cleaning cloth are illustrated. In FIG. 5, for example, an exemplary cloth 454 is illustrated that has an open-mesh type construction. In particular, this exemplary material includes a variety of material strands 455 that are formed into a weaved pattern. As further shown, the weaved pattern creates various pockets 457. In operation, strands 455 of cloth 454 can be engage against materials, skin, and tissue within a user's nose and cause debris to be removed therefrom. The debris may then adhere to strands 455 and/or be captured within pockets 457. As can thus be seen, cloth 454 may thus have a weaved and/or mesh type pattern.

The size, construction, and material of strands 455, and the size and construction of pockets 457 can be varied as desired. In the illustrated example, for instance, strands 455 can be formed of more than one thread. Moreover, while the threads of strands 455 are generally illustrated as following a defined pattern the threads may also extend in many different directions. For instance, threads forming strands 455 can extend randomly, or pseudo-randomly to form. On feature of such type of threads is that strands 455 can thus produce an exfoliating effect. In particular, the random or untamed threads can contact against the interior of the nose and more effectively brush away dead skin, debris, germs, or other materials. The effect may thus be similar to an exfoliating loufa.

To further the exfoliating effect, strands 455 may be formed of a durable material (e.g., a plastic). In some cases, some threads are formed of one material (e.g., a durable or hard material), while other threads are formed from a relatively softer material. By way of example, suitable materials that can be used to form durable and/or softer materials within strands 455, include polymer-based materials (nylons, polyamides, polypropylene, etc.), organic materials (e.g., cotton, wool, etc.) and or any combinations thereof or of any other suitable material. For example, in one embodiment, cloth 454 is an antimicrobial, exfoliating material in which strands 455 are formed of a polyamide-polypropylene combination (approximately 73% polyamide and 27% polypropylene).

The size of strands 455 and/or pockets 457 can also vary in a desired manner. In one example, pockets 457 bordered by strands 455 can be approximately one-sixteenth inch to one-quarter inch in width, although pockets may also have smaller or larger sizes, as desired. For example, pockets may have a square or diamond shape that has sides that are approximately one-eighth inch in length, although pockets may have other shapes, sizes, and configurations. Strands 455 may also be various sizes. For example, strands 455, whether made of one or more threads, may in one embodiment, be between one-thirty second inch and three-thirty seconds inch in width or diameter, although they may have a greater or smaller width or diameter if desired.

Turning now to FIG. 6, another example embodiment of a fabric material is schematically illustrated. In FIG. 6, a cloth 554 is illustrated that also includes a plurality of strands 555 which are woven together to also form a plurality of pockets 557. As can be seen when compared with cloth 454 in FIG. 5, cloth 554 of FIG. 6 has a tighter weave or tighter strand 555 pattern. For example, in this embodiment, strands 555 and pockets 557 have approximately the same width, although this is exemplary only. Moreover, while pockets 557 are shown as having a generally square shape, this isn't necessary, and pockets 557 can be circular, rectangular, or have any other desired shape. For instance, if every other strand 555 along the vertical distance is removed, pockets 557 may have a generally rectangular shape.

As with other nasal cleaning cloths described herein, cloth 554 may also be formed of any suitable material, and strands 555 may have any suitable size. Further, it is not necessary to have strands 555, as cloth 554 need not have a woven construction, but may be otherwise formed. Accordingly, it will be appreciated that cloth 554 may have any suitable design. For example, strands 555 may be sized on the orders of microns or may be larger (e.g., about a quarter inch in width), or anywhere in between. Where desired, strands 555 may also have larger or smaller sizes or, as noted above, strands 555 may be excluded entirely.

The various embodiments disclosed and contemplated herein thus allow users to prevent the onset of illness. In other cases, the user can remove materials to alleviate suffering from allergies, illness and/or asthma. In any case, the removal of these materials facilitates the breathing of cleaner, fresher air. The ease of use allows a user to use the nasal cleaning apparatus daily or as needed to obtain the proper care and cleaning of the nasal cavity through the nostrils. Accordingly, according to aspects of the present invention, a user of the nasal cleaning apparatus can gently and effectively clean his or her nostrils to aid in the prevention or remediation of breathing problems and/or of the flu and chronic sinus problems. The product is further safe and easy to use for people of all ages.

The present invention may be embodied in other specific forms without departing from its spirit or essential characteristics. The described embodiments are to be considered in all respects only as illustrative and not restrictive.

What is claimed is:

1. An apparatus for cleaning a nasal cavity of a user, comprising:
   a grip;
   a head attached to said grip, wherein the head has a distal end and a proximal end; and
   an anti-microbial cleaning cloth attached to said head, wherein the anti-microbial cleaning cloth is folded along a fold line to form a first half and a second half, wherein the head is positioned in an interior portion of the anti-microbial cleaning cloth between the first and second halves with the distal portion of the head being positioned proximate to the fold line and the first and second halves extending toward the proximal end of the head, and wherein said anti-microbial cleaning cloth is configured to be inserted into a nostril of the user, with said head, and remove debris from the nasal cavity of the user.

2. An apparatus as recited in claim 1, wherein said anti-microbial cleaning cloth is draped or wrapped around said head.

3. An apparatus as recited in claim 1, wherein said head has a substantially semi-spherical distal end, and has a contoured external surface such that said head has multiple different diameters along an elongate length thereof.

4. An apparatus as recited in claim 3, wherein a middle portion of said head has a concave contour.

5. An apparatus as recited in claim 3, wherein said distal end and a proximal end of said head have substantially convex contours.

6. An apparatus as recited in claim 1, wherein said grip includes at least one gripping member configured to facilitate handling of said grip.

7. An apparatus as recited in claim 6, wherein said at least one gripping member includes a concave contour on said grip.

8. An apparatus as recited in claim 6, wherein said at least one gripping member includes a plurality of ridges.

9. An apparatus as recited in claim 8, wherein said plurality of ridges extend partially along an elongate length of said grip and are designed for traction.

10. An apparatus as recited in claim 8, wherein said plurality of ridges extend along a portion of said grip having an external concave contour.

11. An apparatus as recited in claim 6, wherein said at least one gripping member includes an actuation mechanism configured to facilitate selectively rotation of said anti-microbial cleaning cloth and said head, the actuation mechanism including at least one of a motor-driven device, a wind-up device, or a gear-driven device configured to selectively drive rotation of the anti-microbial cleaning cloth and the head.

12. An apparatus as recited in claim 1, wherein the folded anti-microbial cleaning cloth is a substantially squared shaped piece of fabric folded along a diagonal line to a first triangular half and a second triangular half, and wherein first and second apex portions of the triangular halves being positioned on opposites sides of the proximal end of the head.

* * * * *